United States Patent [19]

Puskas et al.

[11] 3,954,812

[45] May 4, 1976

[54] POLYBUTENE COMPOSITION CONTAINING HALOGEN-CONTAINING ADDITIVES AND USE THEREOF

[75] Inventors: Imre Puskas, Glen Ellyn; John A. Cengel, Wheaton, both of Ill.

[73] Assignee: Standard Oil Company, Chicago, Ill.

[22] Filed: May 10, 1973

[21] Appl. No.: 358,911

[52] U.S. Cl. .................. 260/346.8 R; 252/182; 252/56 D; 526/74; 526/213
[51] Int. Cl.² ................................ C07D 307/36
[58] Field of Search ............ 260/346.8 R, 78.4 D, 260/537 R; 252/33

[56] References Cited
UNITED STATES PATENTS

| | | | |
|---|---|---|---|
| 2,845,403 | 7/1958 | Gunberg | 260/346.8 R |
| 3,018,250 | 1/1962 | Anderson et al. | 260/346.8 R |

Primary Examiner—Harry I. Moatz
Attorney, Agent, or Firm—Fred R. Ahlers; Arthur G. Gilkes; William T. McClain

[57] ABSTRACT

Viscous polybutenes of number average molecular weight ($\overline{M}_n$) in the range of about 300 to about 3000 have improved reactivity with intramolecular anhydrides of unsaturated aliphatic dicarboxylic acids when such polybutenes contain rather small amounts, i.e., 5 to 200 ppm, of halogenated, preferably chlorinated and/or brominated carboxylic or sulfonic acid. Preference is given to such halogen containing compounds having a sufficient vapor pressure at a temperature in the range of 100° to 300°C to be substantially completely removed at absolute pressures in the range of 5 to 760 mm Hg. Use of such polybutenes containing such halogenated compounds in the addition reaction with said unsaturated anhydrides can reduce formation of undesired tarry product resulting from polymerization and/or thermal decomposition of the unsaturated anhydrides and enhance yield of desired alkenyl-substituted anhydride.

3 Claims, No Drawings

POLYBUTENE COMPOSITION CONTAINING HALOGEN-CONTAINING ADDITIVES AND USE THEREOF

BACKGROUND OF INVENTION

Viscous polybutenes of about 300 to about 3000 $\overline{M}_n$ have viscosities in the range of about 4 to about 5500 centistokes at 100°C. Such polybutenes are commercially available from polymerization of refinery butenes; isobutylene, cis-butene-2 and butene-1 generally present with butane in a $C_4$ fraction. Commercially since about 1940 such $C_4$ fractions with or without added isobutylene, or isobutylene rich concentrates have been polymerized in the presence of Friedel-Crafts catalyst. The wide range in viscosity and in molecular weight depends, as is known, on polymerization temperature, to a lesser extent on catalyst and its concentration, and on the olefin content of the feed. The viscous polybutenes are essentially water white and thermally decompose with no residue at temperatures above 275°C. and have some use applications in engine oils as anti-scuff agents and viscosity index improvers and in fuels for internal combustion engines to reduce or suppress deposits in the fuel induction system.

The viscous polybutenes have also found use as components of caulking compounds, adhesives and electric-cable insulating oils. However, the greatest use of the viscous polybutenes has been as a raw material in the manufacture of addition agents for fuels and gasoline because the viscous polybutenes are reactive olefins and provide branched-chain alkyl structure in derivatives enhancing their solubility in petroleum products such as lubricant oils, fuels and refinery streams. The derivatives of most interest in the past 15 years are from the polybutenyl-substituted intramolecular anhydrides of aliphatic dicarboxylic acids such as succinic anhydride. The polybutenyl-substituted saturated aliphatic anhydrides have been used per se, or as diesters, amides, imides, amidines, imidines, and neutral or overbased basic metal salts as addition agents in petroleum products. The addition agents from polybutenes of $\overline{M}_n$ below 500 are mainly used in fuels; for example in gasoline to inhibit rusting, carburetor deposits, and carburetor icing and in diesel fuels to inhibit rust, corrosion and smoke, and in motor oils and industrial oils as rust and wear inhibitors.

The addition agents from polybutenes of 500 to about 3000 $\overline{M}_n$ have found extensive use as detergent-dispersants in motor oils and lesser use as carburetor detergents in gasoline, heat exchanger antifoulants in refinery streams, rust and corrosion inhibitors in surface coatings and as emulsifiers and demulsifiers.

The viscous polybutenes are complex mixtures of polymers, copolymers and interpolymers of isobutylene, cis-butene-2 and butene-1. The nature and relative amounts of the butene monomers involved in the polymerization leading to a particular $\overline{M}_n$ polybutene are not indicative of the resulting polymer product because extensive isomerization occurs during polymerization. The viscous polybutenes, although largely mono-olefins, may contain 0 to 20% isoparaffins. The unsaturation in the viscous polybutene molecules is predominantly in a terminal or near terminal group which, as later illustrated, are of the trisubstituted or vinylidene type. The non-olefinic chain portion of the polybutene molecules is composed of normal butyl and isobutyl monomer unit and hence is a long and branched alkyl chain. Such long, branched alkyl chain of the lighter (below 500 $\overline{M}_n$) polybutenes contain relatively greater amounts of normal butyl units and lesser amounts of iso-butyl units. The heavier (500-3000 $\overline{M}_n$) polybutenes contain relatively greater amounts of isobutyl units and lesser amounts of normal butyl units which are concentrated near the end of the long, branched alkyl chain. For example, the structures of a polydisperse polybutene of about 900 $\overline{M}_n$ have in part been identified through the use of infrared spectroscopy (calibrated by NMR) and permanganate cleavage. The principal structures identified are shown below (in decreasing order of concentration):

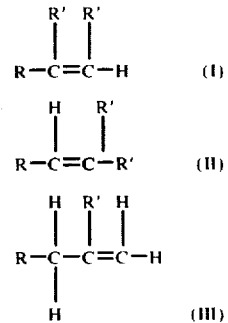

wherein R is the long, branched alkyl chain and comprises about 600 mole % $(C_4)_{4\ to\ 35}$, about 30 mole % $(C_4)_{12\ to\ 35}$ and about 10 mole % $(C_4) > 35$; R' is mainly methyl but is also ethyl; and the ratio of iso-$C_4$ to n-$C_4$ is about 3:1.

With respect to polybutene addition reactivity with unsaturated intramolecular anhydrides, it is believed that the olefinic terminal groups in the three structures shown above are in the decreasing reactivity order of III, I and II. In the uncatalyzed addition reaction, some of the slow reacting molecular species remain unreacted and with the isoparaffinic polymer species (0–20% of the total polymer product) which do not react at all, the desired polybutenyl-substituted saturated anhydride product can be obtained in maximum yields of 75–80% based on starting polymer.

Such addition reaction between the viscous polybutene and intramolecular anhydride of unsaturated aliphatic dicarboxylic acid can typically use any one of maleic anhydride, citraconic anhydride, itaconic anhydride, ethyl maleic anhydride, halo (e.g., chloro-) maleic anhydride, glutaconic anhydride, homomesaconic anhydride, and the like according to U.S. Pat. Nos. 2,628,942 and 2,634,256 among others. The addition reactions are, in general, conducted at temperatures in the range of 150° to 300°C. using polybutene to anhydride molar ratios of reactants in the range of 1.0:1.0–15, generally 1.0:1.05–1.15. In addition to the non-reaction of some olefinic species of polybutene and isoparaffinic entities thereof amounting to a total of up to 40–50% of the polybutene charged, there is also a problem with respect to thermal decomposition and polymerization of the unsaturated anhydride reactant at temperatures upward from 150°C.

Thermal decomposition at temperatures upward from 150°C of unsaturated aliphatic dicarboxylic acids and their anhydrides (e.g., maleic and its anhydride) has been known and is reported, for example, in U.S. Pat. No. 3,476,774 which gives earlier documentation sources therefor. Such thermal decomposition is accompanied by evolution of water vapor and oxides of carbon, in a closed reaction vessel, is accompanied by an increase in internal pressure. Under some observed conditions the thermal decomposition can be so substantially instantaneous as to be explosive. In the absence of explosive thermal decomposition a carbon-containing residue is also formed in addition to water vapor and oxides of carbon. Such thermal decomposition and attendant polymerization of the unsaturated anhydride reactant has been observed as occurring during its addition reaction with polymeric olefins, e.g., polybutenes and others, in a closed reaction vessel. There is the increase of internal pressure by involved water vapor and oxides of carbon (mainly $CO_2$) but the attendant carbon-containing residue varies in nature from somewhat granular when the decomposition is only slight to a tarry material mainly adhering to internal surfaces of the reaction vessel when the decomposition is more extensive but well below explosive magnitude. The granular type residue amounts to from about 0.1 to about 0.3 weight percent of the total charge, in general, is dispersed in the product, the alkenyl-substituted saturated anhydride addition compound diluted with unreacted components of the olefin polymer, is readily separated therefrom by filtration. However, the tarry residual product, which for the most part fouls the internals of the reaction vessel can be as high as 2-3 weight percent of the total charge. The tarry residual material not adhering to reactor internals fouls the filter and interferes with filtration of the desired reaction product. Both types of residue are undesirable because of the above noted fouling characteristics and because their formation results in yield reduction of the desired alkenyl-substituted anhydride addition product.

Various means have been proposed and/or used to suppress thermal conversion of unsaturated anhydride reactant. German Patent No. 1,102,142 for its reaction of triene (e.g., 1,5,9-cyclododecatriene) with maleic anhydride to prepare a 1:1 addition product teaches the use of from 0.01 to 5 weight percent of thionine, phenothiazine, hydroquinone, and related inhibitors. U.S. Pat. No. 3,231,587 teaches the use of chlorine gas in molar amounts equal to maleic anhydride for its addition reaction with olefin polymers (the resulting alkenylsuccinic anhydride contains 0.4–0.5 weight percent chlorine) as a superior to earlier proposed first preparing a chlorinated olefinic polymer having 4–15 weight percent chlorine and reacting the chloropolymer with maleic anhydride. U.S. Pat. No. 3,476,774 teaches the use of a hindered phenol nonreactive with the olefin polymer or maleic anhydride (e.g., 2,6-ditertbutylphenol or 4,4′-methylenebis-2,6-diteri-butylphenol) to suppress thermal decomposition.

Such hindered phenols are not readily removed from the adduct product. The chloro-substituted adduct may not be useful in all cases for the preparation of addition agent derivatives.

In our laboratories the use of small, i.e., catalytic amounts of hydrogen chloride during the adduct formation between olefinic polymer and maleic anhydride achieved success in improving yield and reducing formation of undesired tarry material. A drawback of this method is the possible corrosive nature of stored polybutene. However, it is understood that hydrogen halides can react with the olefinic polymer forming alkyl halide. It is also recognized that at higher temperature, due to decomposition of the alkyl halides, hydrogen halide and halogen formation are possible. Hence it is recognized that addition of trace quantities of hydrogen halide or halogen or alkyl halide to the polymer could achieve the desired improvements in the said reaction. It was also realized that the effectiveness of said halo-compounds will vary with the experimental conditions and the exact chemical nature and concentration of the added material.

From the standpoint of both the manufacturer-merchant of the viscous polybutenes and the purchasers-users thereof it would be desirable to modify such polybutene compositions by addition of a small amount of material which enhances reactivity of the polybutene and suppresses formation of the undesirable tarry material without undesirable added effects. It would be further desirable that such modification of the polybutenes be accomplished by a simple, single process step of not only combining a small amount of material with the polybutene to effect the desired reactivity enhancement and tarry material suppression but also by use of a material which is readily removable from the adduct reaction product. For this latter benefit it is pointed out that unreacted anhydride, including that used in slight molar excess per mole of polybutene, is removed from the adduct reaction product by evaporation at an absolute pressure in the range of 5 to 760 mm Hg. and at a temperature below reaction temperature. Thus it is beneficial to add to the polybutene such material having the above-beneficial effects on the adduct reaction and at the same time readily removable at said temperature and pressure conditions at which unreacted unsaturated anhydride is removed.

SUMMARY OF INVENTION

It has now been discovered that viscous polybutenes of from about 300 to about 3000 $\overline{M}_n$ containing 10 to 200, preferably from 5 to 200 ppm on weight basis of halogenated, more suitably chlorinated and/or brominated carboxylic or sulfonic acids provides a novel, uniquely modified polybutene composition. Such polybutene composition can be reacted at temperatures of 150°–300°C. with unsaturated anhydride without affecting chemical substitution of either the reactants or the adduct product, the halo-acid additive or its decomposition product can be removed from the adduct product under conditions of removing unreacted unsaturated-anhydride, enhances polybutene conversion to adduct, and suppresses tarry material formation.

To be most readily removable with unreacted unsaturated anhydride at 5 to 760 mm Hg., the halo-acid additives combined with viscous polybutene should have sufficient vapor pressure at such pressures to facilitate their removal. Preferred sub-class of the chloro- and/or bromo-carboxylic or sulfonic acid additives should have a normal (atmospheric pressure) boiling point up to 225°C. but can be as low as 40°C.

Typical, but not all-inclusive, of such chlorinated and/or brominated carboxylic or sulfonic acid additives are alpha-halo carboxylic acids, alpha-halo carboxylic acid anhydrides, carboxylic acid halides, alpha-halo carboxylic acid halide, sulfonic acid halide, N-haloamide of such acids or N-haloimide of such acids. Specific members of such halo-carboxylic or sulfonic acids are chloroastic acid, acetylchloride, chloroacetylchloride, N-chloroacetamide, bromoacetic acid, acetylbromide, N-bromacetamide, N-bromo, bromoacetamide, adipylchloride, adiphylbromide, sebacylchloride, sebacylbromide, alpha-chloroadipic acid, alpha-bromoadipic acid, N-bromoadipamide, alpha-chloroadipylchloride, alpha-bromadiphylbromide, 2-bromostearic acid, N-bromostearamide, chloromaleic anydride, bromomaleic anhydride, maleyldibromide, bromosuccinic anhydride, N-bromosuccinicimide, benzoylchloride, benzoylbromide, toluoylchloride, toluoylbromide, N-bromobenzamide, N-chlorobenzamide, phthaloylchlorides, phthaloylbromides, N-chlorophthalimide, N-bromophthalimide, $N_1$, $N_2$-dibromoterephthalamide, cyanuric-chloride, cyanuricbromide, benzenesulfonylchloride, benzenesulfonylbromide, N-bromobenzenesulfonamide, toluenesulfonylchlorides, toluenesulfonylbromides, N-chlorotoluenesulfonamides, N-bromotoluenesulfonamides, and the like.

The reaction between the viscous polybutenes and the anhydrides of unsaturated aliphatic dicarboxylic acids known to the art to be useful for the addition reaction producing alkenyl-substituted saturated anhydride, is conducted commercially in a batchwise or continuous manner in a stirred-tank type autoclave or equivalent reaction vessel providing intimate contact between the reactants. For batchwise operation the reactants are changed to the closed reaction vessel with or without displacing its air with oxygen-free, e.g., nitrogen, atmosphere at ambient pressure. The reactants can be at ambient temperature but the polybutene reactant is usually at an elevated temperature to reduce the time for the reaction mixture to reach reaction temperature. Solid anhydride reactant can be charged alone or dispersed in the polybutene or alone as a melt. The reaction mixture is stirred while being heated to reaction temperature and during reaction.

Continuous conduct of the addition reaction is maintained by charging to the reaction vessel containing the stirred adduct forming reaction mixture a melt of the anhydride reactant and preheated viscous polybutene so that their combined heat supplies the heat input needed during reaction.

Reaction time for batchwise operation is, in general, 4–8 hours. Continuous operation requires, in general, a shorter residence time, for example 1–3 hours.

Thermal decomposition of anhydride reactant, which evolves $CO_2$ and water vapor, causes an undesirable pressure increase as well as formation of undesirable tarry material during the adduct reaction. Such pressure increase, although undesirable, can be used as an indicator of failure to suppress formation of such tarry material by a component of the polybutene composition. The actual extent of formation of such tarry material is, of course, determined gravimetrically after termination of the addition reaction and removal of unreacted anhydride reactant at the before-mentioned pressure in the range of 5 to 750 mm Hg.

The manner and nature of enhanced adduct yield by the polybutene composition comprising a viscous polybutene of about 300 to about 3000 $\overline{M}_n$ and 5 to 200 ppm halogenated carboxylic or sulfonic acid and suppressed formation of undesirable tarry material is not understood. We speculate that isomerization of the olefin double bond to a more reactive species is accomplished under the catalytic effect of traces of decomposition products derived from the halo-carboxylic or sulfonic acid acids. Further, these trace impurities can also act as radical quenchers and inhibit the decomposition and/or polymerization of the unsaturated anhydride to tar.

The use of the present inventive polybutene compositions and the benefits to be derived therefrom in addition reactions with the before-mentioned unsaturated anhydride will now be illustrated using maleic anhydride, the most commonly, commercially used of those anhydride reactants. These examples are conducted with reactant molar ratio of polybutene to maleic anhydride of 1.0:1.1 in a method which closely approaches commercial practice of using stirred-tank type reactions conducted batchwise followed by removal of unreacted maleic anhydride by evaporation and then filtration of the reaction product.

In the following examples there is illustrated the yield enhancing benefits of using chloro- or bromo-substituted carboxylic or sulfonic acid additives. These examples were conducted in small scale reactivity screening tests using a 22 ml volume Parr bomb having a magnetic stirrer. In each illustrative example, 10.0 grams of polybutene and about 1:1 grams of powdered maleic anhydride (MA) to provide a polymer: MA mole ratio of 1.0:1.1 were charged. The air was displaced from the bomb with nitrogen, the bomb sealed and immersed in a 249° oil bath, the reaction mixture stirred for 6 hours, and then sampled.

A weight aliquot portion of each reaction product so produced was chromotographed on silica gel column. The unreacted polybutene was eluted from the column with hexane and determined gravimetrically to allow the calculation of the weight percent of polybutene that reacted with MA. The total tarry product produced was also determined gravimetrically and calculated as weight percent of the total charge (polymer + MA).

In the following examples, there are illustrated the yield enhancing and tar reducing benefits of using chloro- and bromo-substituted carboxylic or sulfonic acids and derivatives. The following table provides the identification of the $\overline{M}_n$ of the polybutene used, its addition agent and concentration in ppm based on polybutene, and adduct yield and the tar percent.

TABLE

| Example Number | Polymer $\overline{M}_n$ | Additive Name | Concentration, ppm Additive | Cl | Br | Adduct, Yield, % | Tar, Wt. % |
|---|---|---|---|---|---|---|---|
| 1 | 914 | None | 0 | 0 | 0 | 66.0 | 1.5 |
| 2 | " | None | 0 | 0 | 0 | 66.4 | 1.1 |
| 3 | " | Sebacychloride | 150 | 43 | 0 | 72.8 | 0.6 |
| 4 | 957 | None | 0 | 0 | 0 | 61.0 | 1.3 |
| 5 | " | None | 0 | 0 | 0 | 59.4 | 1.5 |
| 6 | " | p-Toluenesulfonylchloride | 102 | 19 | 0 | 67.0 | 1.0 |
| 7 | " | Adipylchloride | 177 | 68 | 0 | 63.5 | 2.2 |
| 8 | " | Bromoacetylbromide | 29 | 0 | 23 | 70.6 | 0.6 |
| 9 | " | Acetylbromide | 48 | 0 | 31 | 74.0 | 0.2 |
| 10 | " | 2-Bromostearic Acid | 98 | 0 | 22 | 68.8 | 0.6 |
| 11 | " | Chloromaleic Anhydride | 550 | 130 | 0 | 69.8 | 0.4 |

TABLE-continued

| Example Number | Polymer $\overline{M}_n$ | Additive Name | Concentration, ppm Additive | Cl | Br | Adduct Yield, % | Tar, Wt. % |
|---|---|---|---|---|---|---|---|
| 12 | " | N-Bromosuccinimide | 75 | 0 | 34 | 73.6 | 0.1 |
| 13 | " | Benzoylbromide | 94 | 0 | 41 | 71.8 | 0.2 |
| 14 | " | Cyanuric Chloride | 110 | 64 | 0 | 69.2 | 0.4 |

The foregoing ten illustrative chloro- or bromo-substituted carboxylic or sulfonic acid additives used according to this invention give results typical of their various respective subclasses hereinbefore disclosed. In general, those illustrative additives provided both adduct yield improvement and tar suppression but the bromo-substituted acid, including N-bromosuccinimide additives gave better yield improvement and tar suppression than did the chloro-substituted acid additives and hence the bromine-containing additives are preferred. Most preferred of those additives for this invention are acetylbromide and N-bromosuccinimide.

While the foregoing examples illustrate benefits afforded by present inventive polybutene compositions containing viscous polybutenes having $\overline{M}_n$ of 900–950, the use of other viscous polybutenes in the $\overline{M}_n$ range of about 300 to 3000 will provide polybutene compositions affording yield improvement and tarry material suppression in the manner and nature above illustrated for the maleic anhydride reactions illustrated. Similar benefits can be expected by the use of the present inventive polybutene compositions with other of the before-named unsaturated anhydrides of aliphatic dicarboxylic acids. Furthermore, the use of these inventive additives can be extended to other olefinic compositions (e.g., polypropenes) in their reaction with the unsaturated intramolecular anhydrides of dicarboxylic acids.

Finally, the inventive additives have been found to be equally useful whether they are added to the olefinic polymers, or to the anhydride reactant or to mixtures of the reactants.

What is claimed is:

1. The method of preparing polybutenylsuccinic anhydride which comprises reacting at a temperature in the range of 150° to 300°C from 0.8 to 5.0 moles maleic anhydride per mole of polybutene in the composition consisting essentially of the butylene polymer having a $\overline{M}_n$ in the range of about 300 to about 3000 and 5 to 200 ppm based on the weight of such polymer of acetyl bromide, bromacetylbromide, benzoylbromide, or N-bromosuccinimide.

2. The method of preparing polybutenyl succinic anhydride which comprises reacting at a temperature in the range of 150° to 300°C from 0.8 to 5.0 moles maleic anhydride per mole of polybutene in the composition consisting essentially of the butylene polymer having a $\overline{M}_n$ in the range of 900 to 950 and 5 to 200 ppm based on the weight of such polymer of acetylbromide.

3. The method of preparing polybutenyl succinic anhydride which comprises reacting at a temperature in the range of 150° to 300°C from 0.8 to 5.0 moles maleic anhydride per mole of polybutene in the composition consisting essentially of the butylene polymer having a $\overline{M}_n$ in the range of 900 to 950 and 5 to 200 ppm based on the weight of such polymer of N-bromosuccinimide.

* * * * *